(12) United States Patent
Berme et al.

(10) Patent No.: US 9,568,382 B1
(45) Date of Patent: Feb. 14, 2017

(54) FORCE MEASUREMENT ASSEMBLY WITH DAMPING AND FORCE MEASUREMENT SYSTEM INCLUDING THE SAME

(71) Applicant: Bertec Corporation, Columbus, OH (US)

(72) Inventors: Necip Berme, Worthington, OH (US); Benjamin Robert Hoffman, Columbus, OH (US)

(73) Assignee: Bertec Corporation, Columbus, OH (US)

(*) Notice: Subject to any disclaimer, the term of this patent is extended or adjusted under 35 U.S.C. 154(b) by 0 days.

(21) Appl. No.: 14/866,910

(22) Filed: Sep. 26, 2015

(51) Int. Cl.
*G01D 7/00* (2006.01)
*G01L 5/16* (2006.01)
*A61B 5/103* (2006.01)
*G01M 1/12* (2006.01)

(52) U.S. Cl.
CPC .............. *G01L 5/16* (2013.01); *A61B 5/1036* (2013.01); *A63B 2220/51* (2013.01); *G01M 1/122* (2013.01)

(58) Field of Classification Search
CPC ..... A61B 5/1036; A63B 2220/51; G01L 5/16; G01M 1/122
USPC ...................... 73/862.041–862.046
See application file for complete search history.

(56) References Cited

U.S. PATENT DOCUMENTS

| | | | |
|---|---|---|---|
| 4,785,896 A | * | 11/1988 | Jacobson ............ G01G 3/1402 177/211 |
| 5,431,058 A | * | 7/1995 | Lagier .................... G10K 9/121 310/337 |
| 6,038,488 A | | 3/2000 | Barnes et al. |
| 6,113,237 A | | 9/2000 | Ober et al. |
| 6,152,564 A | | 11/2000 | Ober et al. |
| 6,295,878 B1 | | 10/2001 | Berme |
| 6,354,155 B1 | | 3/2002 | Berme |
| 6,389,883 B1 | | 5/2002 | Berme et al. |
| 6,936,016 B2 | | 8/2005 | Berme et al. |
| 8,181,541 B2 | | 5/2012 | Berme |
| 8,315,822 B2 | | 11/2012 | Berme et al. |
| 8,315,823 B2 | | 11/2012 | Berme et al. |
| D689,388 S | | 9/2013 | Berme |
| D689,389 S | | 9/2013 | Berme |
| 8,543,540 B1 | | 9/2013 | Wilson et al. |
| 8,544,347 B1 | | 10/2013 | Berme |
| 8,643,669 B1 | | 2/2014 | Wilson et al. |

(Continued)

*Primary Examiner* — Max Noori
(74) *Attorney, Agent, or Firm* — The Law Office of Patrick F. O'Reilly III, LLC

(57) ABSTRACT

A force measurement assembly with damping is disclosed herein. The force measurement assembly includes a force measurement surface for receiving at least one portion of a body of a subject; at least one force transducer, the at least one force transducer configured to sense one or more measured quantities and output one or more signals that are representative of forces and/or moments being applied to the force measurement surface of the force measurement assembly by the subject; at least one base member disposed underneath the at least one force transducer or forming a part of the at least one force transducer; and a damping member disposed between the at least one base member and a mounting surface on which the force measurement assembly is disposed. A force measurement system that includes the force measurement assembly with damping is also disclosed herein.

22 Claims, 12 Drawing Sheets

(56) References Cited

U.S. PATENT DOCUMENTS

| | | |
|---|---|---|
| 8,700,569 B1 | 4/2014 | Wilson et al. |
| 8,704,855 B1 | 4/2014 | Berme et al. |
| 8,764,532 B1 | 7/2014 | Berme |
| 8,847,989 B1 | 9/2014 | Berme et al. |
| D715,669 S | 10/2014 | Berme |
| 8,902,249 B1 | 12/2014 | Wilson et al. |
| 8,915,149 B1 | 12/2014 | Berme |
| 9,032,817 B2 | 5/2015 | Berme et al. |
| 9,043,278 B1 | 5/2015 | Wilson et al. |
| 9,066,667 B1 | 6/2015 | Berme et al. |
| 9,081,436 B1 | 7/2015 | Berme et al. |
| 9,168,420 B1 | 10/2015 | Berme et al. |
| 9,173,596 B1 | 11/2015 | Berme et al. |
| 2003/0216656 A1 | 11/2003 | Berme et al. |
| 2008/0228110 A1 | 9/2008 | Berme |
| 2011/0277562 A1 | 11/2011 | Berme |
| 2012/0266648 A1 | 10/2012 | Berme et al. |
| 2012/0271565 A1 | 10/2012 | Berme et al. |
| 2015/0096387 A1 | 4/2015 | Berme et al. |

* cited by examiner

Detail "A"

Detail "B"

Detail "C"

FORCE MEASUREMENT ASSEMBLY WITH DAMPING AND FORCE MEASUREMENT SYSTEM INCLUDING THE SAME

CROSS-REFERENCE TO RELATED APPLICATIONS

Not Applicable

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to force measurement systems. More particularly, the invention relates to a force measurement assembly with damping and a force measurement system including the same.

2. Background and Description of Related Art

Force measurement systems are utilized in various fields to quantify the reaction forces and moments exchanged between a body and support surface. For example, in biomedical applications, force measurement systems are used for gait analysis, assessing balance and mobility, evaluating sports performance, and assessing ergonomics. In order to quantify the forces and moments resulting from the body disposed thereon, the force measurement system includes some type of force measurement device. Depending on the particular application, the force measurement device may take the form of a balance plate, force plate, jump plate, an instrumented treadmill, or some other device that is capable of quantifying the forces and moments exchanged between the body and the support surface.

Force measurement systems are typically mounted inside a room within a building. Due their high degree of measurement sensitivity, the accuracy of the output generated by these measurement systems is often adversely affected by vibrations imparted thereon by the building structure. These vibrations may be caused by mechanical equipment within the building, such as pumps, fans, and chillers, or alternatively, may be caused by external forces acting on the building structure, such as those caused by wind forces or nearby roadways. As such, the measurement accuracy of these highly sensitive measurement instruments is unnecessarily compromised by building vibrations. Also, when force measurement systems are mounted on uneven surfaces or surfaces with undulations, the resulting instability of the measurement instrument often leads to measurement errors (i.e., resulting from the rocking of the measurement instrument). In addition, when force measurement systems are affixedly attached to mounting surfaces that undergo deformation (e.g., a concrete slab of a building that flexes or deforms), the deformation of the mounting surfaces impart similar deformations on the components of the measurement instruments, thereby producing measurement errors.

In addition, the conventional rigid mounting arrangement of force measurement devices frequently results in a deleterious preloading on these devices. This undesirable preloading may permanently deform various components of force measurement devices, which may also reduce the accuracy of the output generated by the force measurement systems.

What is needed, therefore, is a force measurement assembly that is isolated from the vibrations transferred from the surrounding building structure so that the measurement accuracy of the measurement instrument is not undesirably compromised. Moreover, a force measurement assembly is needed that is not subjected to unnecessary preload stresses that adversely affect the measurement components of the instrument. Furthermore, a force measurement system also is needed that includes a force measurement assembly that is sufficiently isolated from building vibrations so as to obviate the effect of these vibrations on the measurement accuracy of the force measurement assembly. In addition, a force measurement assembly is needed that is capable of compensating for undulations on the mounting surface, uneven portions of the mounting surface, and/or a deformation of the mounting surface.

BRIEF SUMMARY OF EMBODIMENTS OF THE INVENTION

Accordingly, the present invention is directed to a force measurement assembly with damping and a force measurement system including the same that substantially obviates one or more problems resulting from the limitations and deficiencies of the related art.

In accordance with one or more embodiments of the present invention, there is provided a force measurement assembly with damping. The force measurement assembly includes a force measurement surface for receiving at least one portion of a body of a subject; at least one force transducer, the at least one force transducer configured to sense one or more measured quantities and output one or more signals that are representative of forces and/or moments being applied to the force measurement surface of the force measurement assembly by the subject; at least one base member disposed underneath the at least one force transducer or forming a part of the at least one force transducer; and a damping member disposed between the at least one base member and a mounting surface on which the force measurement assembly is disposed.

In a further embodiment of the present invention, the force measurement assembly is in the form of a force plate or an instrumented treadmill.

In yet a further embodiment, the at least one base member comprises at least one longitudinal member and at least one transverse member.

In still a further embodiment, the at least one base member has a generally annular shape.

In yet a further embodiment, the at least one base member comprises one or more flanged portions for providing increased structural rigidity.

In still a further embodiment, the damping member comprises a viscoelastic damping member.

In yet a further embodiment, the viscoelastic damping member has a durometer value between 10 and 40 based upon a Shore OOO hardness scale.

In still a further embodiment, the viscoelastic damping member has a durometer value between 10 and 70 based upon a Shore OO hardness scale.

In yet a further embodiment, the viscoelastic damping member has a thickness in a range between approximately one-eighth of an inch and approximately three-quarters of an inch, inclusive.

In still a further embodiment, the thickness range of the viscoelastic damping member is between approximately one-quarter of an inch and approximately one-half of an inch, inclusive.

In yet a further embodiment, the viscoelastic damping member is configured to compensate for at least one of: (i) undulations on the mounting surface, (ii) uneven portions of the mounting surface, (iii) a deformation of the mounting surface, and (iv) vibrations transferred to the force measurement assembly from the mounting surface.

In accordance with one or more other embodiments of the present invention, there is provided a force measurement assembly with viscoelastic damping. The force measurement assembly includes a force measurement surface for receiving at least one portion of a body of a subject; at least one force transducer, the at least one force transducer configured to sense one or more measured quantities and output one or more signals that are representative of forces and/or moments being applied to the force measurement surface of the force measurement assembly by the subject; at least one base member disposed underneath the at least one force transducer or forming a part of the at least one force transducer; and a viscoelastic damping member disposed between the at least one base member and a mounting surface on which the force measurement assembly is disposed.

In a further embodiment of the present invention, the at least one force transducer is in the form of a load cell pylon or a force transducer beam.

In yet a further embodiment, the at least one base member comprises at least one first pair of spaced-apart longitudinal members and at least one second pair of spaced-apart transverse members, each of the spaced-apart transverse members being connected to a respective one of the spaced-apart longitudinal members at a respective opposed end thereof.

In still a further embodiment, the at least one base member comprises one or more channel members with opposed flanged portions for providing increased structural rigidity.

In yet a further embodiment, the viscoelastic damping member has a durometer value between 10 and 40 based upon a Shore OOO hardness scale.

In still a further embodiment, the viscoelastic damping member has a durometer value between 10 and 70 based upon a Shore OO hardness scale.

In yet a further embodiment, the viscoelastic damping member has a thickness in a range between approximately one-eighth of an inch and approximately three-quarters of an inch, inclusive.

In still a further embodiment, the viscoelastic damping member is configured to compensate for at least one of: (i) undulations on the mounting surface, (ii) uneven portions of the mounting surface, (iii) a deformation of the mounting surface, and (iv) vibrations transferred to the force measurement assembly from the mounting surface.

In accordance with yet one or more other embodiments of the present invention, there is provided a force measurement system with damping that comprises a mounting surface and a force measurement assembly disposed on the mounting surface. The force measurement assembly includes a force measurement surface for receiving at least one portion of a body of a subject; at least one force transducer, the at least one force transducer configured to sense one or more measured quantities and output one or more signals that are representative of forces and/or moments being applied to the force measurement surface of the force measurement assembly by the subject; at least one base member disposed underneath the at least one force transducer or forming a part of the at least one force transducer; and a damping member disposed between the at least one base member and the mounting surface on which the force measurement assembly is disposed.

In a further embodiment of the present invention, the damping member comprises a viscoelastic damping member.

In yet a further embodiment, the viscoelastic damping member is configured to compensate for at least one of: (i) undulations on the mounting surface, (ii) uneven portions of the mounting surface, and (iii) a deformation of the mounting surface, and (iv) vibrations transferred to the force measurement assembly from the mounting surface.

In still a further embodiment, the mounting surface comprises a top surface of a mounting plate, the mounting plate being affixed to a floor of the building in which the force measurement assembly is located.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

Figure 1:
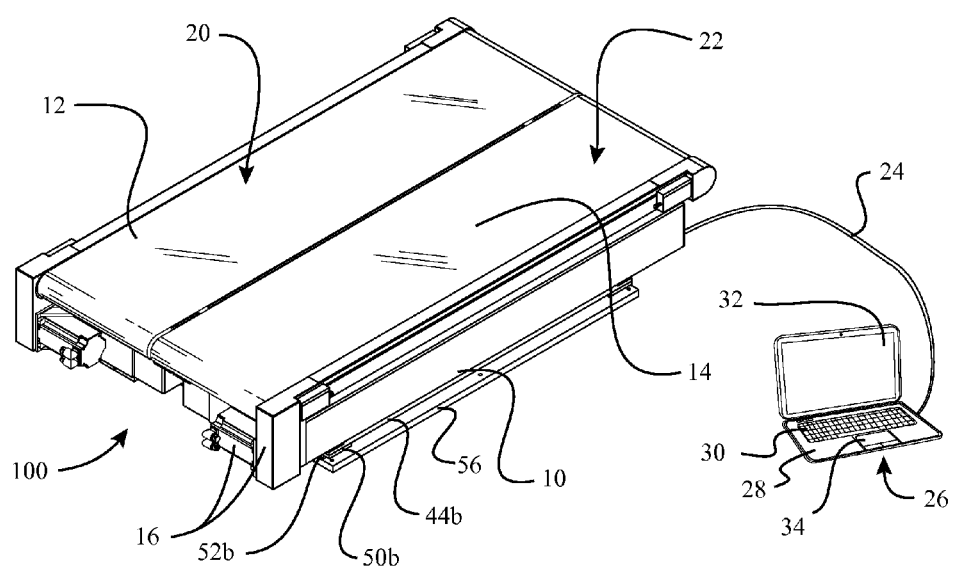
FIG. 1 is a top perspective view of a force measurement system with a force measurement assembly in the form of an instrumented treadmill, according to a first embodiment of the invention, wherein the instrumented treadmill is provided with damping thereunder.
Figure 2:
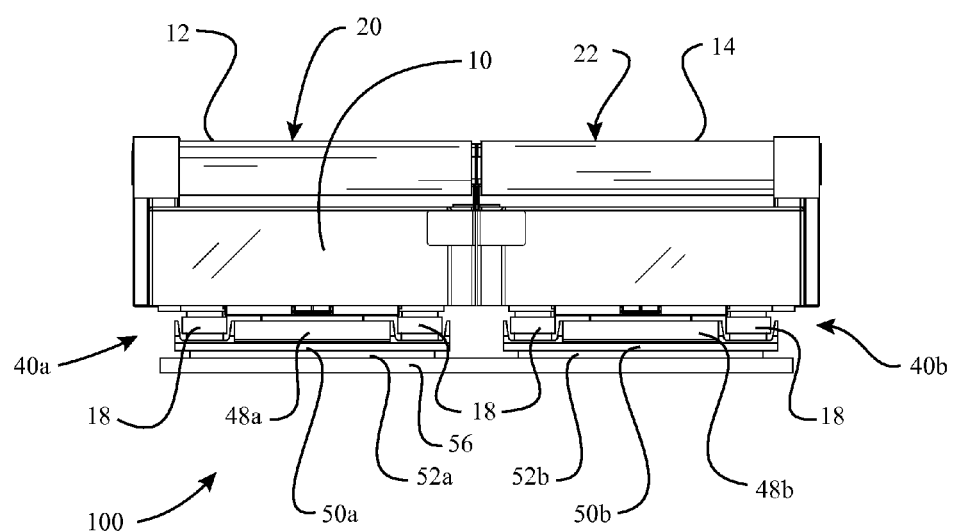
FIG. 2 is a rear end view of the instrumented treadmill with damping of FIG. 1.
Figure 3:
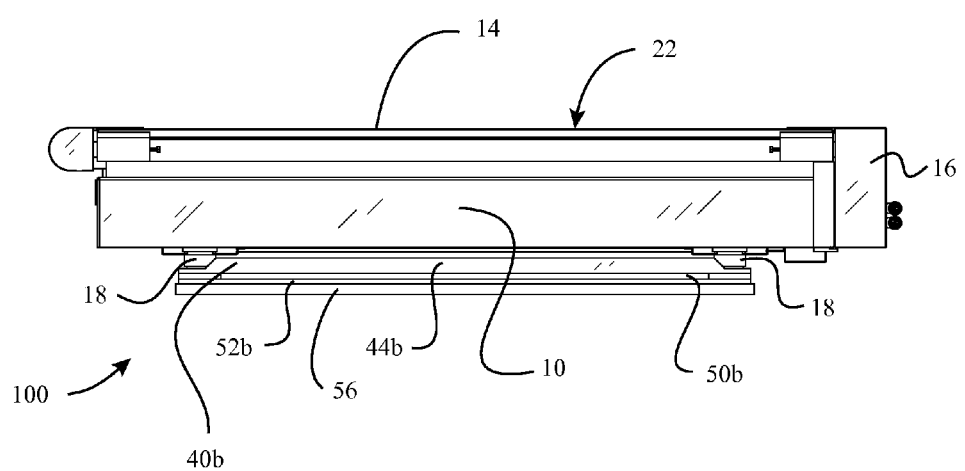
FIG. 3 is a side view of the instrumented treadmill with damping of FIG. 1.
Figure 4:
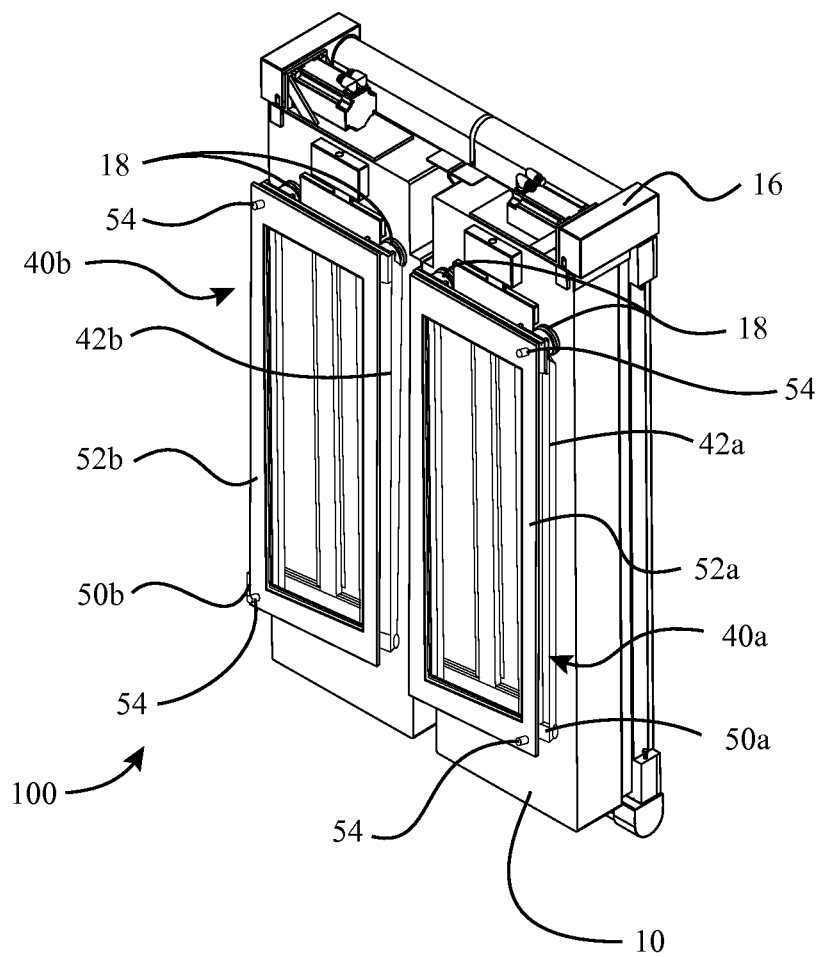
FIG. 4 is a bottom perspective view of the instrumented treadmill with damping of FIG. 1.

A first embodiment of a force measurement system with damping is seen generally at 100 in FIG. 1. The first embodiment of the force measurement system 100 generally comprises a force measurement assembly in the form of an instrumented treadmill 10, which is operatively coupled to a data acquisition/data processing device 26 (i.e., a data acquisition and processing device) by virtue of an electrical cable 24. The instrumented treadmill 10 is configured to receive a subject thereon. As best illustrated in FIGS. 2-4, the instrumented treadmill 10 is attached to the top of a pair of damping assemblies 40a, 40b. The instrumented treadmill 10 has a plurality of top surfaces (i.e., left and right rotating belts 12, 14) that are each configured to receive a portion of a body of a subject (e.g., the left belt 12 of the instrumented treadmill 10 is configured to receive a left leg of a subject, whereas the right belt 14 of the instrumented treadmill 10 is configured to receive a right leg of the subject).

In one or more embodiments, a subject walks or runs in an upright position atop the treadmill 10 with the feet of the subject contacting the respective top surfaces 20, 22 of the treadmill belts 12, 14. The belts 12, 14 of the treadmill 10 are rotated by independent electric actuator assemblies with speed adjustment mechanisms 16. In the illustrated embodiment, each electric actuator assembly and associated speed adjustment mechanism 16 comprises an electric motor with a variable speed control device operatively coupled thereto. Each electric actuator assembly and associated speed adjustment mechanism 16 is capable of rotating its respective treadmill belt 12, 14 at a plurality of different speeds. The speed adjustment mechanisms adjust the speed at which each of their respective treadmill belts 12, 14 are rotated. As mentioned above, the instrumented treadmill 10 is operatively connected to the data acquisition/data processing device 26 by an electrical cable 24. While they are not readily visible in the top perspective view of FIG. 1 due to their location, the instrumented treadmill 10 includes a plurality of force transducers (e.g., four (4) pylon-type force transducers 18—see FIGS. 2-5) disposed below each rotating belt 12, 14 of the treadmill 10 so that the loads being applied to the top surfaces of the belts 12, 14 can be measured. Advantageously, the separated belts 12, 14 of the instrumented treadmill 10 enable the forces and/or moments applied by the left and right legs of the subject to be independently determined. The electrical cable 24 operatively couples both the electric actuator assemblies with speed adjustment mechanisms 16 and the pylon-type force transducers 18 of the instrumented treadmill 10 to the data acquisition/data processing device 26.

As mentioned above, each of the treadmill belts 12, 14 is supported atop four (4) pylon-type force transducers 18 (or pylon-type load cells) that are disposed underneath, and near each of the four corners (4) of the left rotating belt 12 of the treadmill 10 and each of the four corners (4) of the right rotating belt 14 (see FIGS. 2-5). Each of the eight (8) illustrated pylon-type force transducers 18 has a plurality of strain gages adhered to the outer periphery of a cylindrically-shaped force transducer sensing element for detecting the mechanical strain of the force transducer sensing element imparted thereon by the force(s) applied to the belt surfaces 20, 22 of the instrumented treadmill 10. In FIGS. 2 and 3, it can be seen that each of the four (4) sets of pylon-type force transducers 18 are mounted atop respective damping assemblies 40a, 40b so as to prevent building vibrations from adversely affecting the measurement accuracy of the pylon-type force transducers 18. Also, as shown in FIGS. 1-3 and 5, a base plate or mounting plate 56 is provided underneath the damping assemblies 40a, 40b for facilitating the mounting of the instrumented treadmill 10 to a support surface, such as a floor of a building.

In an alternative embodiment, rather than using four (4) pylon-type force transducers 18 on each treadmill belt assembly 12, 14, force transducers in the form of transducer beams could be provided under each treadmill belt assembly 12, 14. In this alternative embodiment, the left treadmill belt assembly 12 could comprise two transducer beams that are disposed underneath, and on generally opposite sides of the treadmill belt assembly 12. Similarly, in this embodiment, the right treadmill belt assembly 14 could comprise two transducer beams that are disposed underneath, and on generally opposite sides of the right treadmill belt assembly 14. Similar to the pylon-type force transducers 18, the force transducer beams could have a plurality of strain gages attached to one or more surfaces thereof for sensing the mechanical strain imparted on the beam by the force(s) applied to the surfaces 20, 22 of the instrumented treadmill 10.

Rather, than using four (4) force transducer pylons under each treadmill belt assembly 12, 14, or two spaced apart force transducer beams under each treadmill belt assembly 12, 14, it is to be understood that the instrumented treadmill 10 can also utilize the force transducer technology described in U.S. Pat. No. 8,544,347, the entire disclosure of which is incorporated herein by reference.

In the illustrated embodiment, the electrical cable 24 is used for the transmission of data between the instrumented treadmill 10 and the data acquisition/data processing device 26. A separate power cable is used to provide power to the instrumented treadmill 10 (e.g., a power cable connected directly to the electrical power system of the building in which the treadmill 10 is disposed). While a hardwired data connection is provided between the instrumented treadmill 10 and the data acquisition/data processing device 26 in the illustrated embodiment, it is to be understood that the instrumented treadmill 10 can be operatively coupled to the data acquisition/data processing device 26 using other signal transmission means, such as a wireless data transmission system.

Referring to the illustrative embodiment of FIG. 1, it can be seen that the data acquisition/data processing device 26 (e.g., in the form of a laptop digital computer) generally includes a base portion 28 with a central processing unit (CPU) disposed therein for collecting and processing the data that is received from the instrumented treadmill 10, and a plurality of devices 30-34 operatively coupled to the central processing unit (CPU) in the base portion 28. Preferably, the devices that are operatively coupled to the central processing unit (CPU) comprise user input devices 30, 34 in the form of a keyboard 30 and a touchpad 34, as well as a graphical user interface in the form of a laptop LCD screen 32. While a laptop type computing system is depicted in FIG. 1, one of ordinary skill in the art will appreciate that another type of data acquisition/data processing device 26 can be substituted for the laptop computing system such as, but not limited to, a palmtop computing device (i.e., a PDA)

or a desktop type computing system having a plurality of separate, operatively coupled components (e.g., a desktop type computing system including a main housing with a central processing unit (CPU) and data storage devices, a remote monitor, a remote keyboard, and a remote mouse).

Now, the acquisition and processing of the load data carried out by the force measurement system will be described. Initially, a load is applied to the instrumented treadmill 10 by a subject disposed thereon. The load is transmitted from the treadmill belt assemblies 12, 14 to its respective set of pylon-type force transducers 18 (or force transducer beams). As described above, in the illustrated embodiment, each treadmill belt assembly 12, 14 comprises four (4) pylon-type force transducers 18 disposed thereunder. Preferably, these pylon-type force transducers 18 are disposed near respective corners of each treadmill belt assembly 12, 14. In a preferred embodiment, each of the pylon-type force transducers 18 includes a plurality of strain gages wired in one or more Wheatstone bridge configurations, wherein the electrical resistance of each strain gage is altered when the associated portion of the associated pylon-type force transducer undergoes deformation resulting from the load (i.e., forces and/or moments) acting on the treadmill belt assemblies 12, 14. For each plurality of strain gages disposed on the pylon-type force transducers 18, the change in the electrical resistance of the strain gages brings about a consequential change in the output voltage of the Wheatstone bridge (i.e., a quantity representative of the load being applied to the measurement surface). Thus, in one embodiment, the four (4) pylon-type force transducers 18 disposed under each treadmill belt assembly 12, 14 output a total of thirty-two (32) raw output voltages (signals) in either analog or digital form. In some embodiments, if the output voltages (signals) are in analog form, the thirty-two (32) raw output voltages (signals) from each treadmill belt assembly 12, 14 are then transmitted to a preamplifier board for preconditioning. The preamplifier board is used to increase the magnitudes of the transducer analog voltages, and preferably, to convert the analog voltage signals into digital voltage signals as well. After which, in one or more embodiments, each treadmill belt assembly 12, 14 transmits the output signals $S_{FPO1}$-$S_{FPO32}$ to a main signal amplifier/converter. Depending on whether the preamplifier board also includes an analog-to-digital (A/D) converter, the force plate output signals $S_{FPO1}$-$S_{FPO32}$ could be either in the form of analog signals or digital signals. The main signal amplifier/converter further magnifies the force plate output signals $S_{FPO1}$-$S_{FPO32}$, and if the signals $S_{FPO1}$-$S_{FPO32}$ are of the analog-type (for a case where the preamplifier board did not include an analog-to-digital (A/D) converter), it may also convert the analog signals to digital signals. Then, the signal amplifier/converter transmits either the digital or analog signals $S_{ACO1}$-$S_{ACO32}$ to the data acquisition/data processing device 26 (computer 26) so that the forces and/or moments that are being applied to the surfaces 20, 22 of the treadmill belts 12, 14 can be transformed into output load values. In addition to hardware components, such as a microprocessor, memory, and data storage device(s), the data acquisition/data processing device 26 may further comprise an analog-to-digital (A/D) converter if the signals $S_{ACO1}$-$S_{ACO32}$ are in the form of analog signals. In such a case, the analog-to-digital converter will convert the analog signals into digital signals for processing by the microprocessor of the data acquisition/data processing device 26.

In one or more embodiments, when the data acquisition/data processing device 26 receives the voltage signals $S_{ACO1}$-$S_{ACO32}$, it initially transforms the signals into output forces and/or moments by multiplying the voltage signals $S_{ACO1}$-$S_{ACO32}$ by a calibration matrix. After which, the force and moment components (i.e., $F_{Lx}$, $F_{Ly}$, $F_{Lz}$, $M_{Lx}$, $M_{Ly}$, $M_{Lz}$) exerted on the left belt surface 20 of the left treadmill belt assembly 12 by the left foot of the subject, the force and moment components (i.e., $F_{Rx}$, $F_{Ry}$, $F_{Rz}$, $M_{Rx}$, $M_{Ry}$, $M_{Rz}$) exerted on the right belt surface 22 of the right treadmill belt assembly 14 by the right foot of the subject, and the center of pressure ($x_{P_L}$, $y_{P_L}$; $x_{P_R}$, $y_{P_R}$) for each foot of the subject (i.e., the x and y coordinates of the point of application of the force applied to the measurement surface by each foot) are determined by the data acquisition/data processing device 26.

Figure 5:
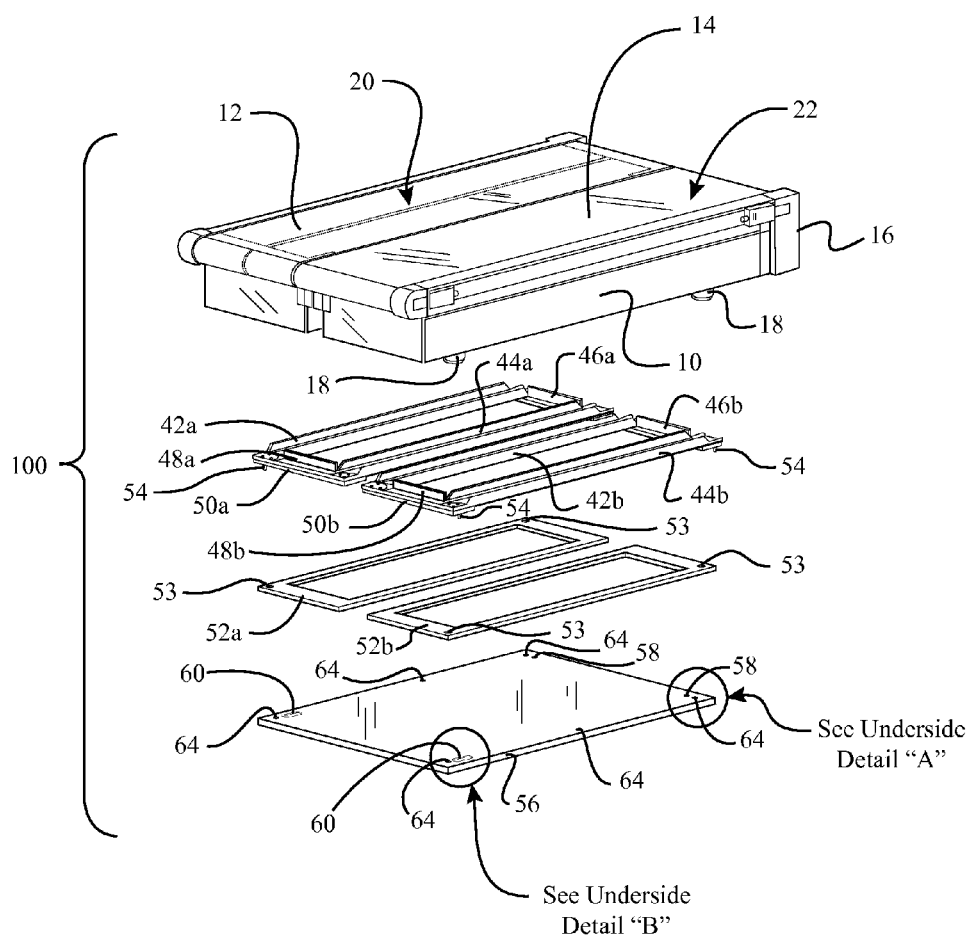
FIG. 5 is an exploded perspective view of the instrumented treadmill with damping of FIG. 1.
Figure 6:
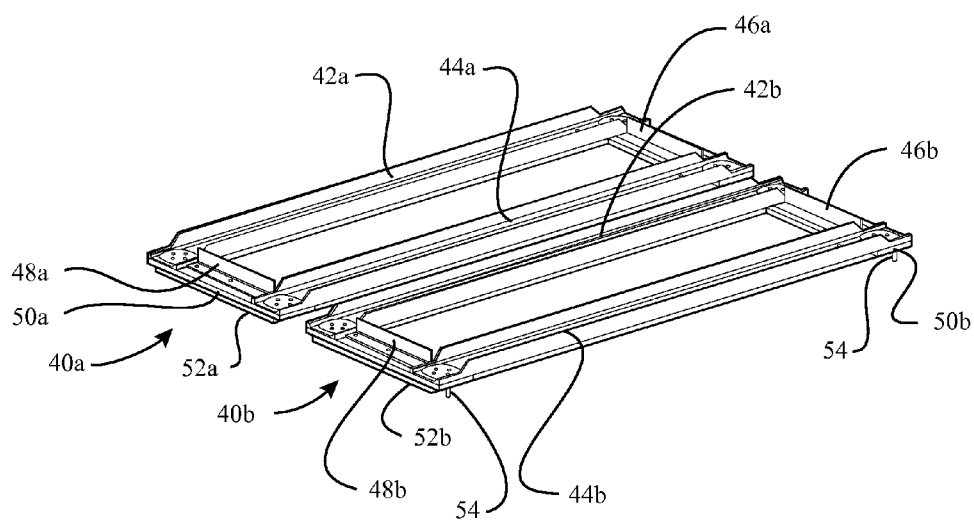
FIG. 6 is a top perspective view of the damping assemblies of the force measurement system of FIG. 1.
Figure 7:
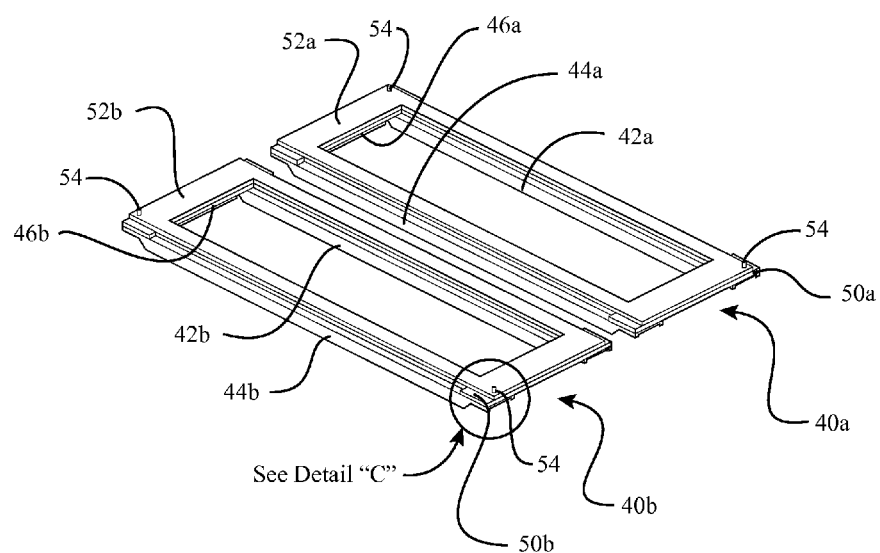
FIG. 7 is a bottom perspective view of the damping assemblies of the force measurement system of FIG. 1.

Now, primarily with reference to FIGS. 5-7, the damping assemblies 40a, 40b disposed under each of the treadmill belt assemblies 12, 14 will be described. As explained above, each of the damping assemblies 40a, 40b is affixed to the bottom side of each of the pylon-type force transducers 18 of the treadmill belt assemblies 12, 14 (e.g., by using suitable fasteners, such as screws or bolts). Initially, as best shown in FIGS. 5 and 6, the illustrative embodiment of the left damping assembly 40a generally comprises a base member subassembly 42a, 44a, 46a, 48a, 50a and an annular damping member 52a disposed underneath the base member subassembly 42a, 44a, 46a, 48a, 50a. In FIG. 6, it can be seen that, in the illustrative embodiment, the base member subassembly 42a, 44a, 46a, 48a, 50a of the left damping assembly 40a comprises a first longitudinal member 42a, a second longitudinal member 44a, a first transverse member 46a, a second transverse member 48a, and an annular base member 50a affixedly attached to, and disposed underneath the longitudinal and transverse members 42a, 44a, 46a, 48a. As depicted in FIGS. 5 and 6, the pair of longitudinal base members 42a, 44a are spaced-apart from one another by a first predetermined distance (i.e., based upon the transverse spacing between the pylon-type force transducers 18), while the pair of transverse base members 46a, 48a are spaced-apart from one another by a second predetermined distance (i.e., based upon the longitudinal spacing between the pylon-type force transducers 18). Also, as most clearly illustrated in FIG. 6, a respective opposed end of each spaced-apart transverse base member 46a, 48a is disposed adjacent to an end portion of one of the spaced-apart longitudinal base members 42a, 44a. In one or more embodiments, the respective opposed ends of each spaced-apart transverse base member 46a, 48a may be connected to an end portion of a respective one of the spaced-apart longitudinal base members 42a, 44a. Also, it can be seen in FIG. 6 that the pair of longitudinal base members 42a, 44a and the pair of transverse base members 46a, 48a may be affixedly mounted to the top surface of the annular base member 50a (e.g., by using a plurality of suitable fasteners, such as screws or bolts, or by welding). In the illustrative embodiment, the annular damping member 52a is affixed to the bottom surface of the annular base member 50a (e.g., by using a suitable adhesive).

In an alternative embodiment, rather than being formed as a separate component subassembly, the base member subassemblies may be formed as parts of the force transducers of the instrumented treadmill 10.

Referring again to FIGS. 5 and 6, the illustrative embodiment of the right damping assembly 40b will now be described. As shown in these two figures, the structural configuration of the right damping assembly 40b is generally the same as the left damping assembly 40a described above. That is, like the left damping assembly 40a, the illustrative embodiment of the right damping assembly 40b generally comprises a base member subassembly 42b, 44b, 46b, 48b, 50b and an annular damping member 52b disposed underneath the base member subassembly 42b, 44b, 46b, 48b, 50b. Similar to the left damping assembly 40a described above, the base member subassembly 42b, 44b, 46b, 48b, 50b of the right damping assembly 40b comprises a first longitudinal member 42b, a second longitudinal member 44b, a first transverse member 46b, a second transverse member 48b, and an annular base member 50b affixedly attached to, and disposed underneath the longitudinal and transverse members 42b, 44b, 46b, 48b. As depicted in FIGS. 5 and 6, the pair of longitudinal base members 42b, 44b are spaced-apart from one another by a first predetermined distance (i.e., based upon the transverse spacing between the pylon-type force transducers 18), while the pair of transverse base members 46b, 48b are spaced-apart from one another by a second predetermined distance (i.e., based upon the longitudinal spacing between the pylon-type force transducers 18). Also, as most clearly illustrated in FIG. 6, a respective opposed end of each spaced-apart transverse base member 46b, 48b is disposed adjacent to an end portion of one of the spaced-apart longitudinal base members 42b, 44b. In one or more embodiments, the respective opposed ends of each spaced-apart transverse base member 46b, 48b may be connected to an end portion of a respective one of the spaced-apart longitudinal base members 42b, 44b. Also, it can be seen in FIG. 6 that the pair of longitudinal base members 42b, 44b and the pair of transverse base members 46b, 48b may be affixedly mounted to the top surface of the annular base member 50b (e.g., by using a plurality of suitable fasteners, such as screws or bolts, or by welding). In the illustrative embodiment, the annular damping member 52b is affixed to the bottom surface of the annular base member 50b (e.g., by using a suitable adhesive).

Once again, with reference to FIGS. 5 and 6, it can be seen that the longitudinal base members 42a, 42b, 44a, 44b and the transverse base members 46a, 46b, 48a, 48b may comprise one or more flanged portions for providing increased structural rigidity. More particularly, as shown in FIG. 6, it can be seen that each of the longitudinal base members 42a, 42b, 44a, 44b may be in the form of channel members with opposed flanged portions for providing increased structural rigidity (i.e., as shown in FIG. 6, a majority of the length of each longitudinal base member 42a, 42b, 44a, 44b may be provided with a U-shaped cross-sectional shape for enhancing the structural rigidity thereof). Specifically, the U-shaped cross-sectional shape of the longitudinal base members 42a, 42b, 44a, 44b provides enhanced rigidity in both the Y-plane, and in the Z-plane. Also, as shown in FIG. 6, it can be seen that each of the transverse base members 46a, 46b, 48a, 48b may be in the form of an L-shaped flange member for providing enhanced structural rigidity. Advantageously, the use of the U-shaped longitudinal base members 42a, 42b, 44a, 44b and the L-shaped transverse base members 46a, 46b, 48a, 48b provides increased structural rigidity, while minimizing the weight associated with the longitudinal base members 42a, 42b, 44a, 44b and the transverse base members 46a, 46b, 48a, 48b by reducing the required thickness of these members 42a, 42b, 44a, 44b, 46a, 46b, 48a, 48b (i.e., the flange portions of these members obviate the need for thick cross-sections). As such, the overall masses of the left and right damping assemblies 40a, 40b are capable of being minimized by utilizing the U-shaped longitudinal base members 42a, 42b, 44a, 44b and the L-shaped transverse base members 46a, 46b, 48a, 48b.

In an exemplary embodiment, the longitudinal base members 42a, 42b, 44a, 44b, the transverse base members 46a, 46b, 48a, 48b, and the annular base members 50a, 50b may be formed from a suitable metallic material that is sufficiently strong and rigid, such as steel or aluminum.

In the illustrative embodiment, the damping members 52a, 52b comprise viscoelastic damping members. More particularly, in the illustrative embodiment, the damping members 52a, 52b may be formed from a synthetic viscoelastic urethane polymer that, while being a solid polymer in form, functions like a quasi-liquid. That is, the synthetic viscoelastic urethane polymer is readily deformed by an applied force and is slow to recover from the force applied thereto. In one or more embodiments, the viscoelastic damping members 52a, 52b may have a durometer value between 10 and 40 based upon a Shore OOO hardness scale. More particularly, in one or more embodiments, the viscoelastic damping members 52a, 52b may have a durometer value between 18 and 35 based upon a Shore OOO hardness scale. In one or more other embodiments, the viscoelastic damping members 52a, 52b may have a durometer value between 10 and 70 based upon a Shore OO hardness scale. In addition, in one or more embodiments, the viscoelastic damping members 52a, 52b may have a thickness in a range between approximately one-eighth of an inch and approximately three-quarters of an inch, inclusive (or between one-eighth of an inch and three-quarters of an inch, inclusive). More particularly, in one or more embodiments, the viscoelastic damping members 52a, 52b may have a thickness range between approximately one-quarter of an inch and approximately one-half of an inch, inclusive (or range between one-quarter of an inch and one-half of an inch, inclusive). Because the durometer hardness value and the thickness value for the damping members 52a, 52b governs the effectiveness of the damping that is provided, these above-described ranges have an important effect on the functionality of the damping assemblies 40a, 40b.

As shown in FIGS. 1-3 and 5, the viscoelastic damping member 52a is disposed between the left base member subassembly 42a, 44a, 46a, 48a, 50a and the mounting plate 56, while the viscoelastic damping member 52b is disposed between the right base member subassembly 42b, 44b, 46b, 48b, 50b and the mounting plate 56. The viscoelastic damping members 52a, 52b are configured to absorb vibrations transferred to the pylon-type force transducers 18 from the mounting plate 56. The vibrations imparted on the mounting plate 56 originate from the building in which the instrumented treadmill 10 is located, and may be caused by other pieces of mechanical equipment disposed inside the building that vibrate, such as pumps, fans, etc. Alternatively, the vibrations imparted on the mounting plate 56 may originate from other sources of vibrations acting on the building (e.g., vibrations imparted by wind forces, adjoining roads, etc.). As shown in the exploded view of FIG. 5, the mounting plate 56 may be provided with a plurality of fastener apertures 64 for affixing the mounting plate 56 to a floor of a building in which the instrumented treadmill 10 is located. As an alternative, or in addition to, using a plurality of fasteners to affix the mounting plate 56 to a floor of a building, a suitable adhesive may be used to affix the mounting plate 56 to the floor of the building.

Advantageously, in addition to absorbing vibrations transferred to the pylon-type force transducers 18 from the mounting plate 56, the viscoelastic damping members 52a, 52b also compensate for undulations on the mounting surface (e.g., the top surface of the mounting plate 56) and uneven portions of the mounting surface (e.g., the top surface of the mounting plate 56). The viscoelasticity of the damping members 52a, 52b enables the damping members 52a, 52b to compensate for the undulations and/or uneven portions of the mounting surface by filling in the gaps or valleys in the mounting surface. Another advantage of the viscoelastic damping members 52a, 52b is that they compensate for the deformation or flexing of the mounting surface. For example, in one or more embodiments, the mounting plate 56 may be affixed to the concrete slab of a building floor. The concrete slab of the building floor may deform or flex when a force is applied thereto (e.g., when a person is walking around the instrumented treadmill 10). Because the mounting plate 56 of the instrumented treadmill 10 is rigidly affixed to the building concrete slab, the deformation or flexing of the building concrete slab results in a consequential deformation of the mounting plate 56. The viscoelastic damping members 52a, 52b prevent the deformation of the mounting plate 56 from imparting a similar deformation on the pylon-type force transducers 18 of the instrumented treadmill 10 by isolating the pylon-type force transducers 18 from the mounting plate 56 (i.e., the viscoelasticity of the damping members 52a, 52b allows the damping members 52a, 52b to fill in the small gap between the mounting plate 56 and the instrumented treadmill 10 that is created by the deformation). As such, advantageously, the pylon-type force transducers 18 of the instrumented treadmill 10 are unaffected by the deformation of the building concrete slab and the mounting plate 56, thereby preventing any measurement errors resulting from the deformation of the building concrete slab.

Figure 8:
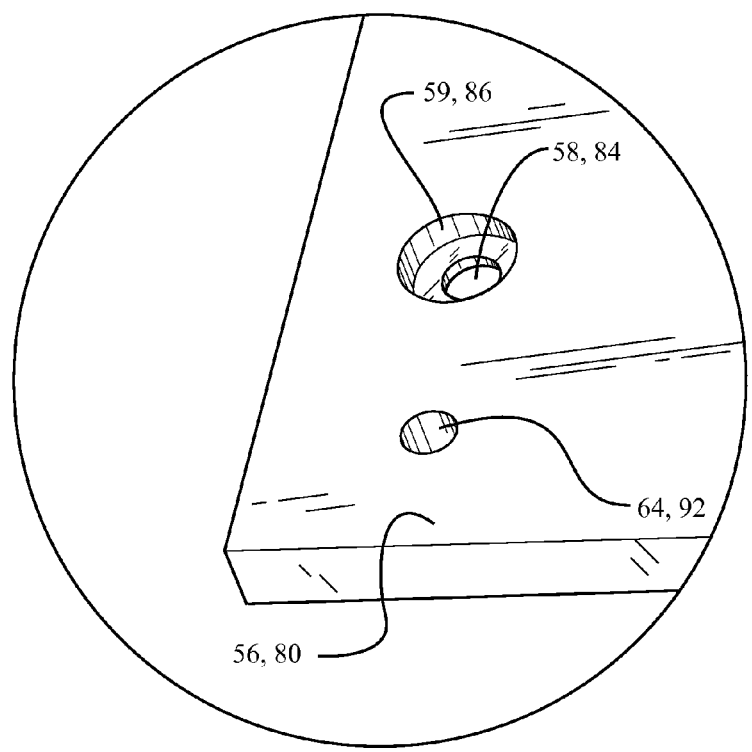
FIG. 8 is an enlarged detail view of the counterbore surrounding one of the circular apertures in the mounting plate of the instrumented treadmill assembly and the force plate (Detail "A")
Figure 9:
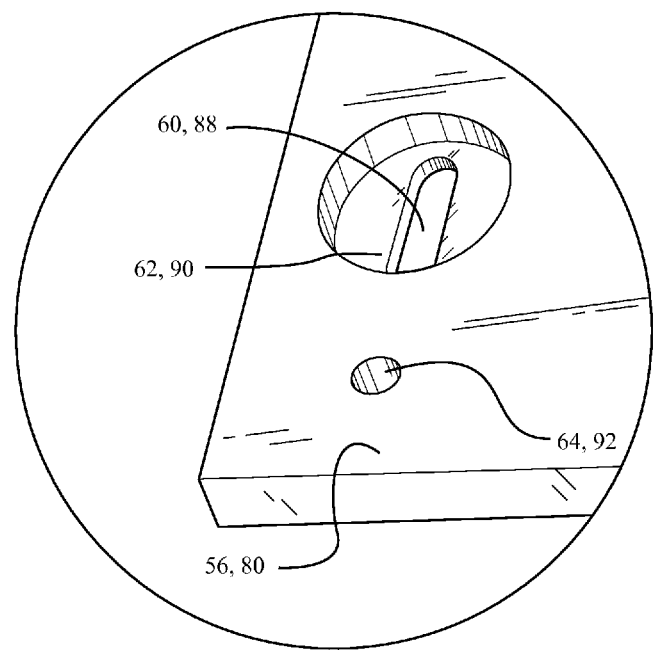
FIG. 9 is an enlarged detail view of the counterbore surrounding one of the elongate slots in the mounting plate of the instrumented treadmill assembly and the force plate (Detail "B")

Referring collectively to FIGS. 4 and 5, it can be seen that respective alignment pins 54 are provided at each of the two outside corners on the opposite ends of the left base member subassembly 42a, 44a, 46a, 48a, 50a and at each of the two outside corners on the opposite ends of the right base member subassembly 42b, 44b, 46b, 48b, 50b. More particularly, in the illustrated embodiment, one pair of alignment pins 54 is affixedly attached to the underside of the longitudinal member 42a and extends through a pair of corresponding apertures 53 in the viscoelastic damping member 52a, while the other pair of alignment pins 54 is affixedly attached to the underside of the longitudinal member 44b and extends through a pair of corresponding apertures 53 in the viscoelastic damping member 52b. Each of the alignment pins 54 extends beneath the bottom surface of the viscoelastic damping members 52a, 52b and is received within a respective aperture 58 or slot 60 disposed in the mounting plate 56. More particularly, as shown in the illustrated embodiment of FIG. 5, the two (2) alignment pins 54 at the front end of the instrumented treadmill 10 engage corresponding circular apertures 58 in the mounting plate 56, while the two (2) alignment pins 54 at the rear end of the instrumented treadmill 10 engage corresponding elongate slots 60 in the mounting plate 56. The alignment pins 54 connect the left base member subassembly 42a, 44a, 46a, 48a, 50a and the right base member subassembly 42b, 44b, 46b, 48b, 50b to the mounting plate 56 without overly constraining the instrumented treadmill assembly, which could potentially result in measurement errors in the force and moment measurements. The two (2) alignment pins 54 at the front end of the instrumented treadmill 10, which are received within the circular apertures 58 of the mounting plate 56, constrain the instrumented treadmill 10 in the X and Y directions, while the two (2) alignment pins 54 at the rear end of the instrumented treadmill 10, which are received within the elongate slots 60 of the mounting plate 56, only constrain the instrumented treadmill 10 in X direction. Referring to the detail view of FIG. 8, a circular counterbore 59 is provided around each of the circular apertures 58 on the underside of the mounting plate 56. Similarly, referring to the detail view of FIG. 9, a circular counterbore 62 is also provided around each of the elongate slots 60 on the underside of the mounting plate 56. The counterbores 59, 62 help to prevent moments from being developed in instrumented treadmill assembly, which could introduce undesirable measurement errors. Because it is not practically possible for the pins 54 to be perfectly aligned within their respective apertures 58 and slots 60 in the mounting plate 56, the counterbores 59, 62 are provided to prevent measurement errors resulting from these misalignments by permitting the lower portions of the alignment pins 54 to be essentially unconstrained within the mounting plate 56. While the instrumented treadmill assembly is provided with a total of four (4) alignment pins 54 in the illustrative embodiment, it is to be understood that, in other embodiments, the instrumented treadmill assembly may be provided with more than four (4) alignment pins 54. For example, in one such other embodiment, the instrumented treadmill assembly may be provided with a total of eight (8) alignment pins 54 (i.e., one pin 54 in each corner of the left viscoelastic damping assembly 40a and one pin 54 in each corner of the right viscoelastic damping assembly 40b).

In the illustrative embodiment, the alignment pins 54 generally do not constrain the instrumented treadmill 10 in the Z direction. As a result, the instrumented treadmill 10, the pylon-type force transducers 18, and the left and right base member subassemblies 42a, 42b, 44a, 44b, 46a, 46b, 48a, 48b, 50a, 50b disposed thereunder generally "float" atop the viscoelastic damping members 52a, 52b, which are disposed between the left and right base member subassemblies 42a, 42b, 44a, 44b, 46a, 46b, 48a, 48b, 50a, 50b and the mounting plate 56. However, while the alignment pins 54 of the illustrative embodiment generally do not constrain the instrumented treadmill 10 in the Z direction, it is to be understood that, in an alternative embodiment, each of the pins 54 could be provided with a head portion that is received within the counterbore 59, 62 of the mounting plate 56 so as to constrain the instrumented treadmill 10 in the Z direction. Also, in the alternative embodiment, rather than using pins 54 with heads, shoulder screws or shoulder bolts may be used in place of the pins 54 to attach the instrumented treadmill assembly to the mounting plate 56.

In an alternative embodiment, the viscoelastic damping members 52a, 52b of the instrumented treadmill 10 may be disposed directly on the top of the building floor (e.g., a building concrete slab), rather than using the mounting plate 56. In this alternative embodiment, each of the alignment pins 54 may be received within respective bores within the building floor. The substantial weight of the instrumented treadmill 10 compresses the viscoelastic damping members 52a, 52b, and prevents the instrumented treadmill 10 from shifting or rocking on the building floor. In yet another alternative embodiment, the viscoelastic damping members 52a, 52b of the instrumented treadmill 10 may be disposed on the top of a motion base that is configured to translate and/or rotate the instrumented treadmill 10 and a subject disposed thereon (e.g., the viscoelastic damping members 52a, 52b are sandwiched between the base of the instrumented treadmill 10 and the top surface of the motion base).

Figure 10:
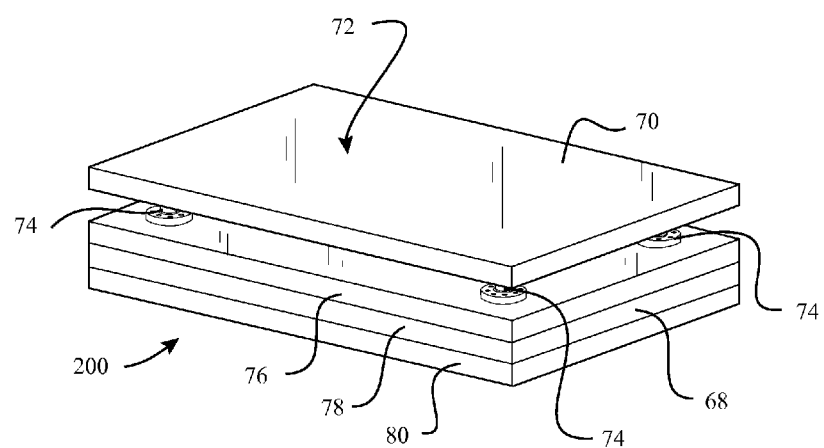
FIG. 10 is a top perspective view of a force measurement system with a force measurement assembly in the form of a force plate, according to a second embodiment of the invention, wherein the force plate is provided with damping thereunder.
Figure 11:
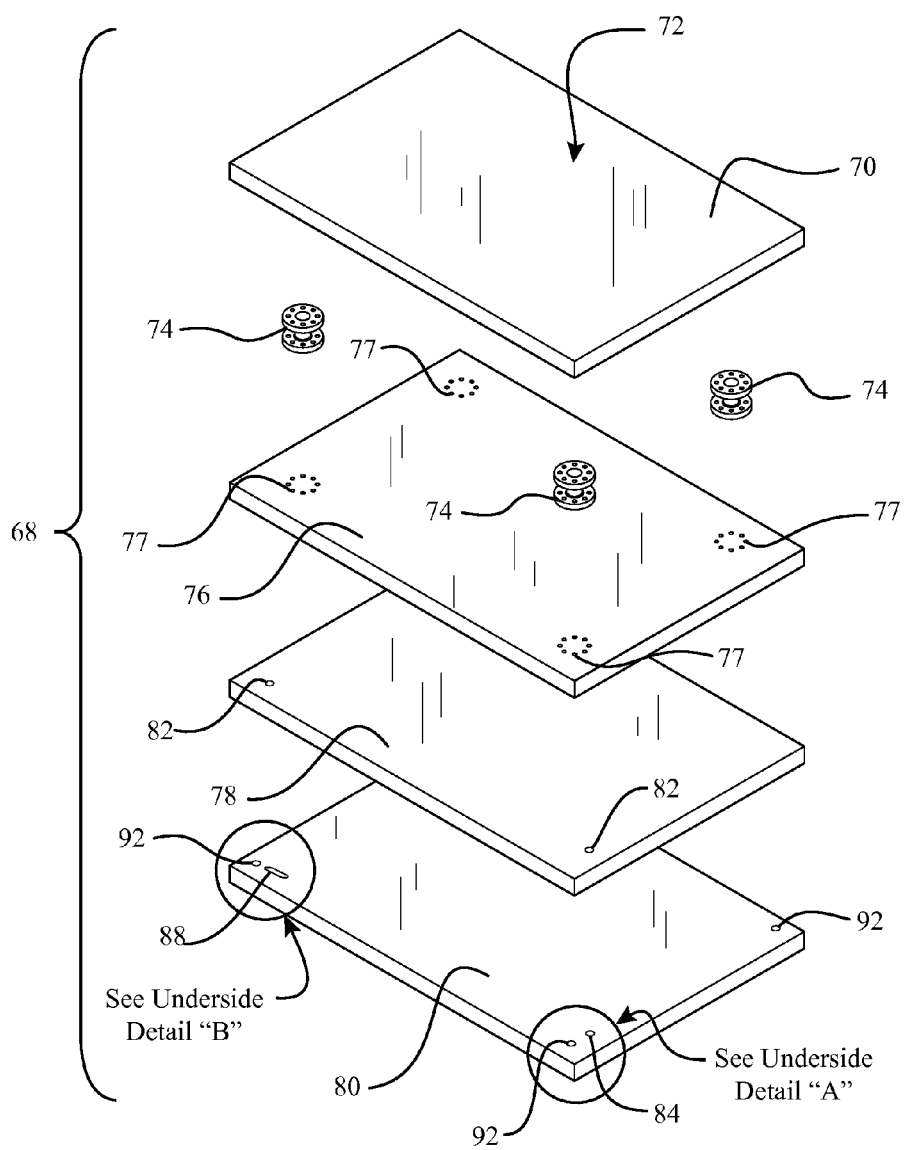
FIG. 11 is an exploded perspective view of the force plate with damping of FIG. 10.
Figure 12:
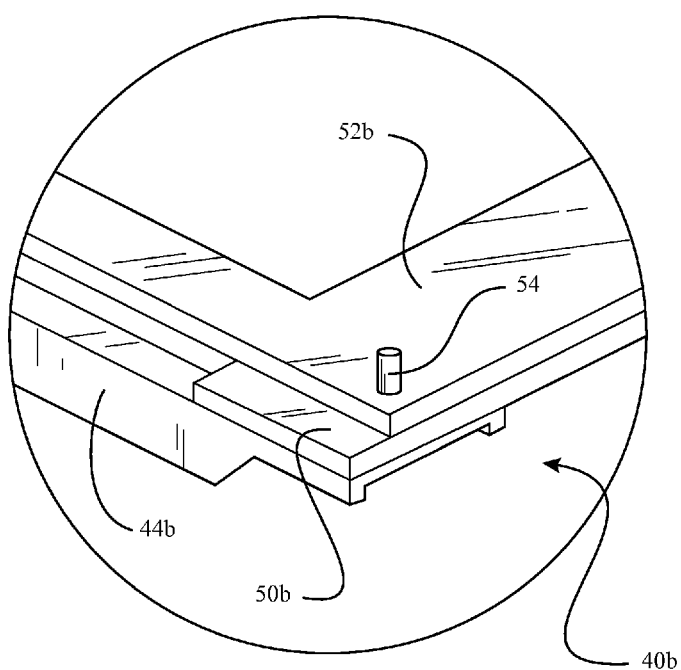
FIG. 12 is an enlarged detail view of an alignment pin at one corner of one of the damping assemblies of the force measurement system of FIG. 1 (Detail "C").

In a further embodiment, with reference to FIGS. 10 and 11, a modified version of the force measurement system 200 with damping may comprise a force measurement device in the form of force plate mounted atop a damping assembly configured to absorb vibrations transferred to the force measurement assembly 68 from the mounting surface (i.e., from the floor of the building). Like the instrumented treadmill 10 described above, the force plate is configured to receive a subject thereon. As shown in FIGS. 10 and 11, the force plate comprises a top plate 70 mounted atop a plurality of force transducers (e.g., four (4) pylon-type force transducers 74) so that the loads being applied to the top surface 72 of the plate component 70 can be measured. In the illustrated embodiment, each of the four (4) pylon-type force transducers 74 (or pylon-type load cells) is disposed underneath, and near a respective one of the four corners (4) of the plate component 70 of the force plate. As described above for the pylon-type force transducers 18, each of the four (4) pylon-type force transducers 74 has a plurality of strain gages adhered to the outer periphery of a cylindrically-shaped force transducer sensing element for detecting the mechanical strain of the force transducer sensing element imparted thereon by the force(s) applied to the top surface 72 of the plate component 70. The output signals from each of the four (4) pylon-type force transducers 74 of the force plate are processed in the same manner as that described above for the instrumented treadmill 10. In addition, like the force measurement system 100 described above, the force measurement system 200 may also comprise a acquisition/data processing device (e.g., in the form of a laptop digital computer) for performing the signal processing functionality described above in conjunction with instrumented treadmill system.

Referring again to FIGS. 10 and 11, the damping subassembly disposed underneath the force plate will be described. In the assembled perspective view of FIG. 10, it can be seen that the damping subassembly is affixed to the bottom side of each of the pylon-type force transducers 74 of the force plate (e.g., by using suitable fasteners, such as screws or bolts). In particular, in an exemplary embodiment, the upper plate member 76 of the viscoelastic damping subassembly may affixed to each of pylon-type force transducers 74 using eight (8) screws connecting the bottom flange of each pylon-type force transducer 74 to the top surface of the upper plate member 76 (and passing through apertures 77 in upper plate member 76). Also, as depicted in the assembled view of FIG. 10, it can be seen that a damping member 78 (i.e., a sheet of damping material) is sandwiched between the upper plate member 76 and the lower mounting plate 80. In the illustrative embodiment, like the damping members 52a, 52b described above, the sheet-like damping member 78 comprises a viscoelastic damping material. The viscoelastic damping material forming the damping member 78 may have the same material properties as that described above for the damping members 52a, 52b (i.e., the same thickness ranges and durometer value ranges described above). In the illustrative embodiment, the sheet-like damping member 78 is affixed to the bottom surface of the upper plate member 76 (e.g., by using a suitable adhesive).

Similar to that described above for the viscoelastic damping members 52a, 52b of the force measurement system 100, the viscoelastic damping member 78 of the illustrated embodiment of FIGS. 10 and 11 is configured to absorb vibrations transferred to the pylon-type force transducers 74 from the lower mounting plate 80. The vibrations imparted on the lower mounting plate 80 originate from the building in which the force plate is located, and may be caused by other pieces of mechanical equipment disposed inside the building that vibrate, such as pumps, fans, etc. Alternatively, the vibrations imparted on the lower mounting plate 80 may originate from other sources of vibrations acting on the building (e.g., vibrations imparted by wind forces, adjoining roads, etc.). The lower mounting plate 80 may be affixed to the floor of a building using a suitable adhesive. As an alternative, or in addition to, using a suitable adhesive to affix the lower mounting plate 80 to a floor of a building, a plurality of fasteners may be used for affixing the lower mounting plate 80 to a floor of a building in which the force plate is located (i.e., each fastener may be received through a respective one of the plurality of fastener apertures 92 in lower mounting plate 80).

Also, as described above for the instrumented treadmill 10, the viscoelastic damping member 78 of the force plate assembly is capable of additionally compensating for undulations on the mounting surface, uneven portions of the mounting surface, and/or a deformation of the mounting surface on which the force measurement assembly is disposed.

Similar to that described above for the longitudinal base members 42a, 44b, in the illustrated embodiment of FIGS. 10 and 11, alignment pins may be provided at two outside corners on the opposite ends of the upper plate member 76. More particularly, in the illustrated embodiment, one pair of alignment pins is affixedly attached to the underside of the upper plate member 76 and extends through a pair of corresponding apertures 82 in the viscoelastic damping member 78. Each of the alignment pins extends beneath the bottom surface of the viscoelastic damping member 78 and is received within a respective aperture 84 or slot 88 disposed in the lower mounting plate 80 (see FIG. 11). The alignment pins connect the force plate damping subassembly to the lower mounting plate 80 without overly constraining the force plate, which could potentially result in measurement errors in the force and moment measurements. The alignment pin at the one end of the force plate assembly, which is received within the circular aperture 84 of the lower mounting plate 80, constrains the force plate in the X and Y directions, while the alignment pin at the other end of the force plate, which is received within the elongate slot 88 of the lower mounting plate 80, only constrains the force plate in X direction. Referring to the detail view of FIG. 8 (which is typical for the two illustrative embodiments described herein), similar to that described above for the instrumented treadmill embodiment, a circular counterbore 86 is provided around the circular pin aperture 84 on the underside of the lower mounting plate 80. Similarly, referring to the detail view of FIG. 9 (which is typical for the two illustrative embodiments described herein), a circular counterbore 90 is also provided around the elongate slot 88 on the underside of the lower mounting plate 80. The counterbores 86, 90 help to prevent moments from being developed in force plate assembly, which could introduce undesirable measurement errors. Because it is not practically possible for the pins to be perfectly aligned within their respective aperture 84 and slot 88 in the lower mounting plate 80, the counterbores 86, 90 are provided to prevent measurement errors resulting from these misalignments by permitting the lower portions of the alignment pins to be essentially unconstrained within the lower mounting plate 80. While the force plate assembly is provided with two (2) alignment pins in the illustrative embodiment, it is to be understood that, in other embodiments, the force plate assembly may be provided with more than two (2) alignment pins. For example, in one such other embodiment, the force plate assembly may be provided with a total of four (4) alignment pins (i.e., one pin in each corner of upper plate member 76).

Similar to that described above, in the illustrative embodiment, the alignment pins generally do not constrain the force plate assembly in the Z direction. As a result, the top plate component 70, the pylon-type force transducers 74, and the upper plate member 76 disposed thereunder generally "float" atop the viscoelastic damping member 78, which is disposed between the upper plate member 76 and the lower mounting plate 80. However, while the alignment pins of the illustrative embodiment generally do not constrain the force plate in the Z direction, it is to be understood that, in an alternative embodiment, each of the pins could be provided with a head portion that is received within the counterbores 86, 90 of the lower mounting plate 80 so as to constrain the force plate in the Z direction. Also, in the alternative embodiment, rather than using pins with heads, shoulder screws or shoulder bolts may be used in place of the pins to attach the force plate assembly to the lower mounting plate 80.

It is readily apparent from the above detailed description that the force measurement systems 100, 200 significantly advance the technical fields of biomechanics and gait analysis by resulting in a force measurement system with increased measurement accuracy. First of all, the force measurement assemblies 10, 68 described above are provided with damping assemblies that effectively isolate the force measurement assemblies 10, 68 from the vibrations transferred from the surrounding building structure, thereby obviating the deleterious effect that these building vibrations have on the measurement accuracy of the measurement instrument. Moreover, because of the manner in which they are mounted to the mounting plates 56, 80, these force measurement assemblies are not subjected to unnecessary preload stresses that adversely affect the measurement components of the instrument. For example, the pylon-type force transducers 18, 74 are not unnecessarily prestressed by the use of rigid fasteners and mounting arrangements. As such, the pylon-type force transducers 18, 74 are not undesirably mechanically deformed prior to the force measurement assembly being loaded (e.g., by forces applied by a subject disposed thereon). Furthermore, the force measurement systems 100, 200 described above are sufficiently isolated from building vibrations so as to obviate the effect that these vibrations have on the measurement accuracy of the force measurement assemblies 10, 68. In addition, advantageously, the viscoelastic damping members 52a, 52b, 78 of the force measurement systems 100, 200 described above are also capable of compensating for undulations on the mounting surface, uneven portions of the mounting surface, and/or a deformation of the mounting surface on which the force measurement assemblies are disposed, thereby enhancing the structural stability of the force measurement assemblies. Also, in one or more embodiments, the force measurement systems 100, 200 are not configured to damp any vibrations transferred from the instrumented treadmill or the force plate to the building structure (e.g., the force measurement system 100 is not configured to damp any vibrations generated by the instrumented treadmill and transferred to the building structure).

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A force measurement assembly with damping, comprising:
a force measurement surface for receiving at least one portion of a body of a subject;
at least one force transducer, the at least one force transducer including a transducer frame element, the at least one force transducer configured to sense one or more measured quantities and output one or more signals that are representative of forces and/or moments being applied to the force measurement surface of the force measurement assembly by the subject;
at least one base member disposed underneath the at least one force transducer or forming a part of the at least one force transducer; and
a damping member disposed between the at least one base member and a mounting surface on which the force measurement assembly is disposed, the damping member being a separate component from the at least one force transducer;
wherein the force measurement assembly is in the form of a force plate or an instrumented treadmill.

2. The force measurement assembly according to claim 1, wherein the at least one base member comprises at least one longitudinal member and at least one transverse member.

3. The force measurement assembly according to claim 2, wherein the at least one base member has a generally annular shape.

4. The force measurement assembly according to claim 1, wherein the at least one base member comprises one or more flanged portions for providing increased structural rigidity.

5. The force measurement assembly according to claim 1, wherein the damping member comprises a viscoelastic damping member.

6. The force measurement assembly according to claim 5, wherein the viscoelastic damping member has a durometer value between 10 and 40 based upon a Shore OOO hardness scale.

7. The force measurement assembly according to claim 5, wherein the viscoelastic damping member has a durometer value between 10 and 70 based upon a Shore OO hardness scale.

8. The force measurement assembly according to claim 5, wherein the viscoelastic damping member has a thickness in a range between approximately one-eighth of an inch and approximately three-quarters of an inch, inclusive.

9. The force measurement assembly according to claim 8, wherein the thickness range of the viscoelastic damping member is between approximately one-quarter of an inch and approximately one-half of an inch, inclusive.

10. The force measurement assembly according to claim 5, wherein the viscoelastic damping member is configured to compensate for at least one of: (i) undulations on the mounting surface, (ii) uneven portions of the mounting surface, (iii) a deformation of the mounting surface, and (iv) vibrations transferred to the force measurement assembly from the mounting surface.

11. A force measurement assembly with viscoelastic damping, comprising:

a force measurement surface for receiving at least one portion of a body of a subject;

at least one force transducer, the at least one force transducer configured to sense one or more measured quantities and output one or more signals that are representative of forces and/or moments being applied to the force measurement surface of the force measurement assembly by the subject;

at least one base member disposed underneath the at least one force transducer or forming a part of the at least one force transducer, the at least one base member comprising at least one first pair of spaced-apart longitudinal members and at least one second pair of spaced-apart transverse members, each of the spaced-apart transverse members being connected to a respective one of the spaced-apart longitudinal members at a respective opposed end thereof; and a viscoelastic damping member disposed between the at least one base member and a mounting surface on which the force measurement assembly is disposed.

12. The force measurement assembly according to claim 11, wherein the at least one force transducer is in the form of a load cell pylon or a force transducer beam.

13. The force measurement assembly according to claim 11, wherein the at least one base member comprises one or more channel members with opposed flanged portions for providing increased structural rigidity.

14. The force measurement assembly according to claim 11, wherein the viscoelastic damping member has a durometer value between 10 and 40 based upon a Shore OOO hardness scale.

15. The force measurement assembly according to claim 11, wherein the viscoelastic damping member has a durometer value between 10 and 70 based upon a Shore OO hardness scale.

16. The force measurement assembly according to claim 11, wherein the viscoelastic damping member has a thickness in a range between approximately one-eighth of an inch and approximately three-quarters of an inch, inclusive.

17. The force measurement assembly according to claim 11, wherein the viscoelastic damping member is configured to compensate for at least one of: (i) undulations on the mounting surface, (ii) uneven portions of the mounting surface, (iii) a deformation of the mounting surface, and (iv) vibrations transferred to the force measurement assembly from the mounting surface.

18. A force measurement system with damping, comprising:

a mounting surface; and a force measurement assembly disposed on the mounting surface, the force measurement assembly being in the form of a force plate or an instrumented treadmill, and the force measurement assembly including:

a force measurement surface for receiving at least one portion of a body of a subject;

at least one force transducer, the at least one force transducer including a transducer frame element, the at least one force transducer configured to sense one or more measured quantities and output one or more signals that are representative of forces and/or moments being applied to the force measurement surface of the force measurement assembly by the subject;

at least one base member disposed underneath the at least one force transducer or forming a part of the at least one force transducer; and a damping member disposed between the at least one base member and the mounting surface on which the force measurement assembly is disposed, the damping member being a separate component from the at least one force transducer.

19. The force measurement system according to claim 18, wherein the damping member comprises a viscoelastic damping member.

20. The force measurement system according to claim 19, wherein the viscoelastic damping member is configured to compensate for at least one of: (i) undulations on the mounting surface, (ii) uneven portions of the mounting surface, (iii) a deformation of the mounting surface, and (iv) vibrations transferred to the force measurement assembly from the mounting surface.

21. The force measurement system according to claim 18, wherein the mounting surface comprises a top surface of a mounting plate, the mounting plate being affixed to a floor of the building in which the force measurement assembly is located.

22. The force measurement system according to claim 18, wherein the mounting surface comprises a top surface of a floor of the building in which the force measurement assembly is located.

* * * * *